(12) United States Patent
Dannan

(10) Patent No.: US 8,027,710 B1
(45) Date of Patent: Sep. 27, 2011

(54) IMAGING SYSTEM FOR ENDOSCOPIC SURGERY

(76) Inventor: Patrick Dannan, Webster Groves, MO (US)

( * ) Notice: Subject to any disclaimer, the term of this patent is extended or adjusted under 35 U.S.C. 154(b) by 1375 days.

(21) Appl. No.: 11/338,980

(22) Filed: Jan. 25, 2006

Related U.S. Application Data

(60) Provisional application No. 60/648,349, filed on Jan. 28, 2005.

(51) Int. Cl.
*A61B 5/05* (2006.01)
(52) U.S. Cl. .................. 600/407; 600/410; 600/409
(58) Field of Classification Search .................. 600/407, 600/410, 420, 431, 476, 478, 473
See application file for complete search history.

(56) References Cited

U.S. PATENT DOCUMENTS

| | | | |
|---|---|---|---|
| 5,441,059 A | 8/1995 | Dannan | |
| 5,662,111 A | 9/1997 | Cosman | |
| 5,716,326 A | 2/1998 | Dannan | |
| 5,749,830 A * | 5/1998 | Kaneko et al. | 600/160 |
| 6,246,898 B1 * | 6/2001 | Vesely et al. | 600/424 |
| 2002/0122113 A1 * | 9/2002 | Foote | 348/48 |
| 2003/0055410 A1 * | 3/2003 | Evans et al. | 606/1 |
| 2003/0214580 A1 * | 11/2003 | Iddan | 348/81 |

OTHER PUBLICATIONS

Krupa et al (Autonomous 3-D positioning of surgical instruments in robotized laparoscopic surgery using visual servoing, IEEE Transactions on robotics and automation, vol. 19, No. 5, Oct. 2003.*
Alexandre Krupa—IEEE Transactions on Robotics and Automation, vol. 19, No. 5, Oct. 2003—"Autonomous 3-D Positioning of Surgical Instruments in Robotized Laparoscopic Surgery Using Visual Servoing"—pp. 842-853.

* cited by examiner

*Primary Examiner* — Tse Chen
*Assistant Examiner* — Joel F Brutus
(74) *Attorney, Agent, or Firm* — Polster, Lieder, Woodruff & Lucchesi, L.C.

(57) ABSTRACT

An imaging system is provided for use with minimally invasive surgery. The imaging system comprises a platform which is anchored to a wall of a patient cavity. The platform comprises a plurality of transceivers which transmit energy toward the surgical site and receive reflected energy. The transceivers transmit rasterized image information to a computer which then displays the image information in real time, enabling a surgeon to view the surgical site on a display device. The transceivers can transmit and receive different types of energy, and the computer can then combine image information from the various different energy types to provide overlaid images of the surgical site. In addition, the computer controls the relative positions of the transceivers so that the images provided to the surgeon will not be affected by movement of the platform or by movement of structures (i.e., organs) at the surgical site.

22 Claims, 3 Drawing Sheets

IMAGING SYSTEM FOR ENDOSCOPIC SURGERY

CROSS-REFERENCE TO RELATED APPLICATIONS

The application claims priority to U.S. Provisional App. No. 60/648,349 filed Jan. 28, 2005 and which is incorporated herein by reference.

STATEMENT REGARDING FEDERALLY SPONSORED RESEARCH OR DEVELOPMENT

Not Applicable.

BACKGROUND OF THE INVENTION

This application relates to imaging systems for use in devices for use in minimally invasive or endoscopic surgery.

Endoscopic or minimally invasive surgery has become fairly common and is becoming more and more common as surgeons learn and advance endoscopic technology and techniques. Currently, endoscopic surgery is used for procedures conducted in the sinus cavities, on the spine, on knees, on feet, in the abdominal cavity, and in the thoracic cavity. As the technology (i.e., the surgical instruments) and techniques advance, endoscopic surgery will become even more prevalent.

Minimally invasive or endoscopic surgery, as is known, is conducted in a cavity within the patient's body. The cavity can be the patient's abdominal cavity, thoracic cavity, or a cavity formed using a tissue lifter. The cavity is closed. Hence, the surgeon is provided means to view the surgical site. In typical endoscopic procedures (such as conducted in the abdomen), an endoscope is used to provide lighting and to view the surgical site. The typical endoscope includes a stiff tube which is inserted into the patient cavity. The tube extends through the patient's tissue (i.e., through the abdominal wall for an abdominal procedure) and extends into the cavity. The end of the endoscope is spaced slightly from the inner surface of the cavity wall. Because of this spacing, the endoscope can pivot about the incision. If the endoscope pivots, the field of view changes. As can be appreciated, a changing field of view can adversely impact an ongoing procedure.

Imaging systems (such as stereotactical systems) have been provided, for example, for brain or cranial surgery. Such systems rely on a previously taken image and compare the previously taken image with a current image such that the surgeon can display the positioning of a surgical tool within the cranium. An example of such a system is described in U.S. Pat. No. 5,662,111. Such systems are acceptable for cranial surgery, where the surgical site is relatively immovable. However, in surgical sites, such as the abdominal or thoracic cavities, for example, where the tissues are softer and movement of the tissues at the surgical site or movement of the cavity wall during a procedure are likely, such stereotactical systems will not work well.

BRIEF SUMMARY OF THE INVENTION

The present invention relates to an imaging system for providing practitioners with an image of a surgical site within a patient cavity during minimally invasive surgery. An illustrative embodiment of the imaging system comprises (a) a plurality of sensors and transmitters adapted to be anchored to a wall of the cavity; b) a plurality of lasers operable to direct a laser beam towards the surgical site; c) means for converting the data from the sensors into image data; and d) means for comparing the image data from two or more sensors to align the image data from the sensors to produce a single unified image. The transmitters are operable to emit a selected form of energy towards the surgical site and the sensors receive reflected energy from the surgical site. The sensors then emit data indicative of the information detected by the sensors. This data is received by a CPU which converts the data into image data. The image data is then output to a display device for viewing by a practitioner, such as a surgeon. The viewing device can, for example, be a screen (i.e., a monitor), a heads-up display (which displays the images on goggles or glasses worn by the practitioner) or any other type of display now known or which is later developed. The data can include intra-corporeal information, such as optical information, thermal information, ultrasonic information, infrared information, Doppler information, spectrographic information, distance information, and combinations thereof. In addition to the intra-corporeal information noted, the data can also include extra-corporeal information, such as x-ray data, CT scan data, MRI data, ultrasound data and combinations thereof.

BRIEF DESCRIPTION OF THE SEVERAL VIEWS OF THE DRAWINGS

Corresponding reference numerals will be used throughout the several figures of the drawings.

DETAILED DESCRIPTION OF THE INVENTION

Figure 1:
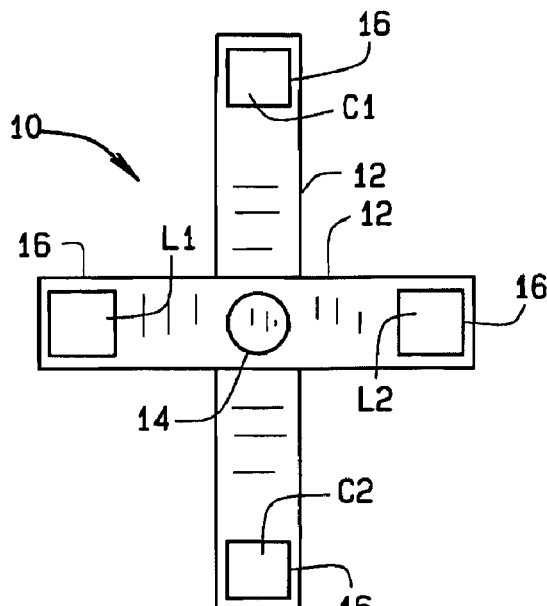
FIG. 1 is a schematic drawing of an instrument platform for use with the imaging system of the present invention.

The following detailed description illustrates the invention by way of example and not by way of limitation. This description will clearly enable one skilled in the art to make and use the invention, and describes several embodiments, adaptations, variations, alternatives and uses of the invention, including what I presently believe is the best mode of carrying out the invention. Additionally, it is to be understood that the invention is not limited in its application to the details of construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

An illustrative embodiment of an imaging system 5 of the present invention includes a platform 10 which is anchored inside a patient cavity, a CPU 18 and a viewing device or display 20. The viewing device can for example, be a screen (i.e., a monitor), a heads-up display (which displays the images on goggles or glasses worn by the practitioner) or any other type of display now known or which is later developed. The platform 10 can be inserted and anchored in the patient cavity as described in my co-pending application Ser. No.

11/006,862, filed Dec. 8, 2004, and which is incorporated herein by reference. Depending on the size and shape of the cavity, the platform 10 can include two arms 12. The two arms are connected together at a connection point 14 and can be pivoted relative to each other to be moved from a collapsed position in which the two arms are parallel to each other for insertion into and removal from the patient cavity, and an expanded position, in which the two arms intersect each other. The platform 10 can comprise a single arm 12 so that the platform can be received in narrow cavities, such as might be formed for spinal surgery. The actual shape of the platform can be varied, as can the number of arms, depending on the size and shape of the cavity in which the platform is to be used. Thus, the arms can have a shape that is other than rectangular, and the platform can have 1, 2 or more arms.

Figure 2A:
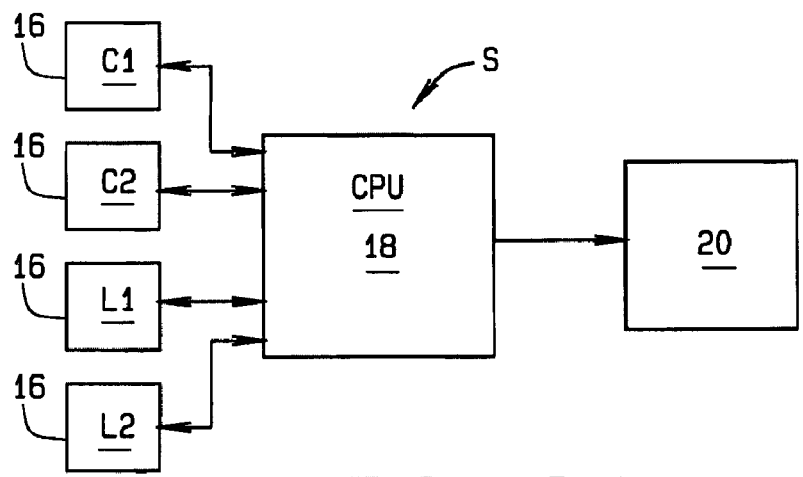
FIG. 2A is a block-diagram drawing of the imaging system of the present invention.
Figure 2B:
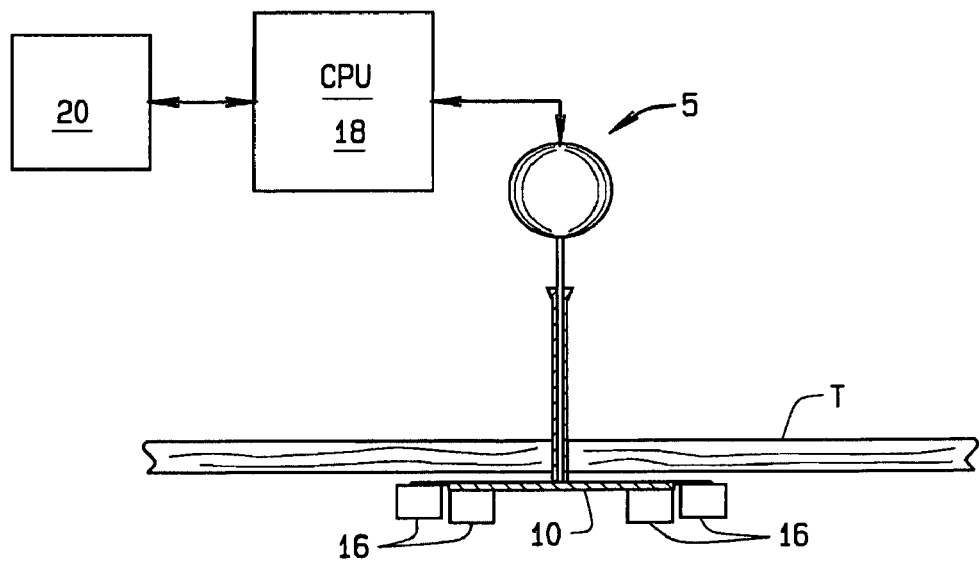
FIG. 2B is a schematic drawing of the imaging system, with the platform anchored on a cavity wall.

The platform is provided with at least one, and preferably, a plurality of devices 16. The devices 16 include transmitters, receivers and or transceivers (collectively, transceivers). The transceivers are operatively connected to a computer or CPU 18 (FIG. 2) to transmit data to the CPU and receive instructional signals from the CPU. As will be described below, the CPU processes the data received from the transceivers to produce a visual image which can then be displayed on a display 20.

Figure 3:
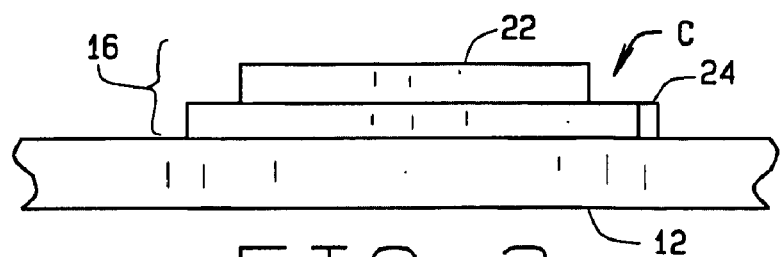
FIG. 3 is a schematic side-elevational drawing of a transceiver for the imaging system.

In the Figures, the platform 10 is shown with two devices 16 on each arm, with the devices being positioned at the ends of the arms. However, more devices can, if desired be positioned on each arm, and a device could be positioned in the center of the platform 10, i.e., at the intersection of the two arms, as well. Turning to FIG. 3, each device 16 is preferably comprises a chip C on which a transceiver 22 is mounted. The device 16 is also provided with micro-electro-mechanical systems (MEMS) 24. The MEMS 24 is in communication with the CPU 18 to be controlled by the CPU 18. Using the MEMS 24, the orientation of the transceiver 22 on the device 16 can be altered by as much as 6°-7°.

Figure 4:
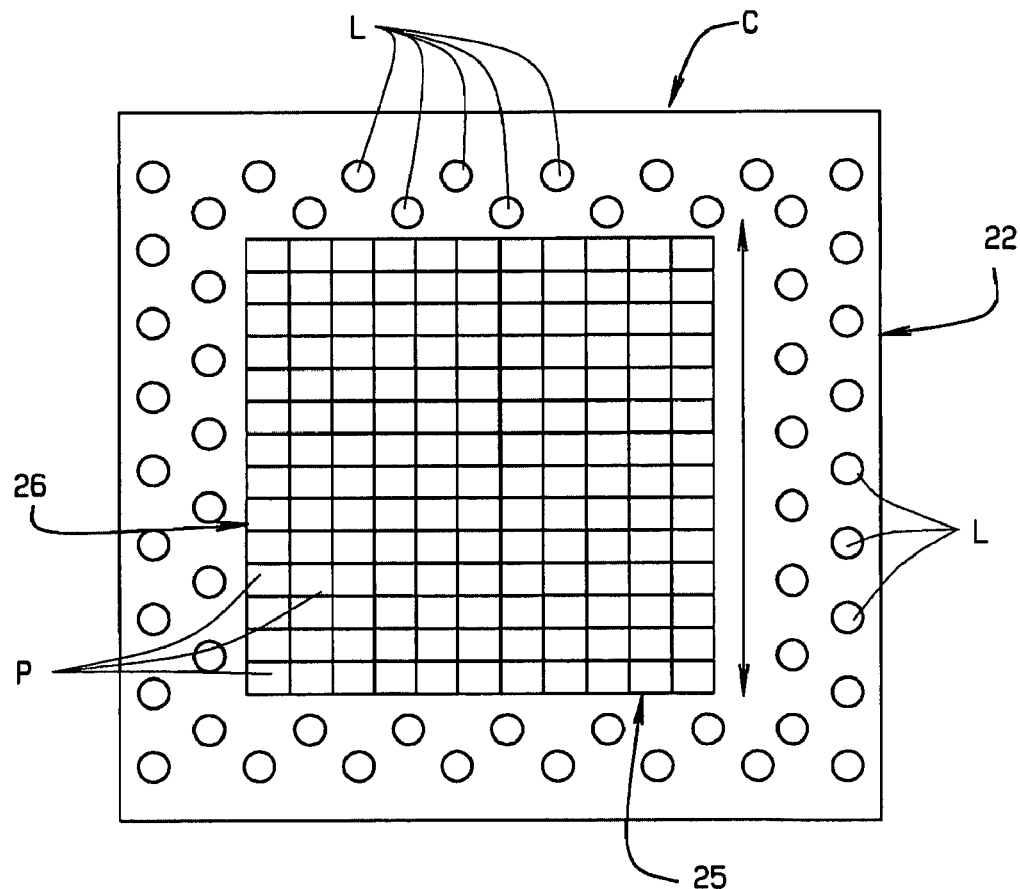
FIG. 4 is a schematic plan view of the transceiver.

Referring to FIG. 4, the transceiver 22 is comprised of a sensor portion 25 comprised of a plurality of pixels P in a pixel array 26. Although the pixel array is shown with slightly more than one hundred pixels, it will be understood that the pixel array can have many thousands or even millions of pixels in its array. In addition, the transceiver 22 includes a plurality of light devices L which surround the pixel array 26. The light devices include lasers (such as VCSEL (Vertical Cavity Surface Emitting Lasers)) or LEDs, which, as discussed below will be used for tracking purposes. In addition, the light devices can include illuminating devices, such as LEDs which will transmit visible light, and are used to illuminate the surgical site. Hence, the transceiver 22 could include both lasers and LEDs. The LEDs could be replaced with other types of illuminating devices which can be positioned either on the chip C, or on the platform arms 12. For example, optic fibers can be used to provide illumination. Such optic fibers would extend along the arm and terminate at the bottom surface of the arm such that the light from the optic fibers would be directed downwardly from the arm. The fiber optics would be operatively connected to an optic fiber extending through an anchor shaft (described below) at the connection point on the platform. The optic fiber in the anchor shaft would then be operatively connected to a light source. Light would then be transmitted through the anchor shaft optic fiber and to the platform arm optic fibers to illuminate the surgical site. It will be appreciated that other types of lighting devices can be used to illuminate the cavity in which the platform 10 is positioned.

Figure 5:
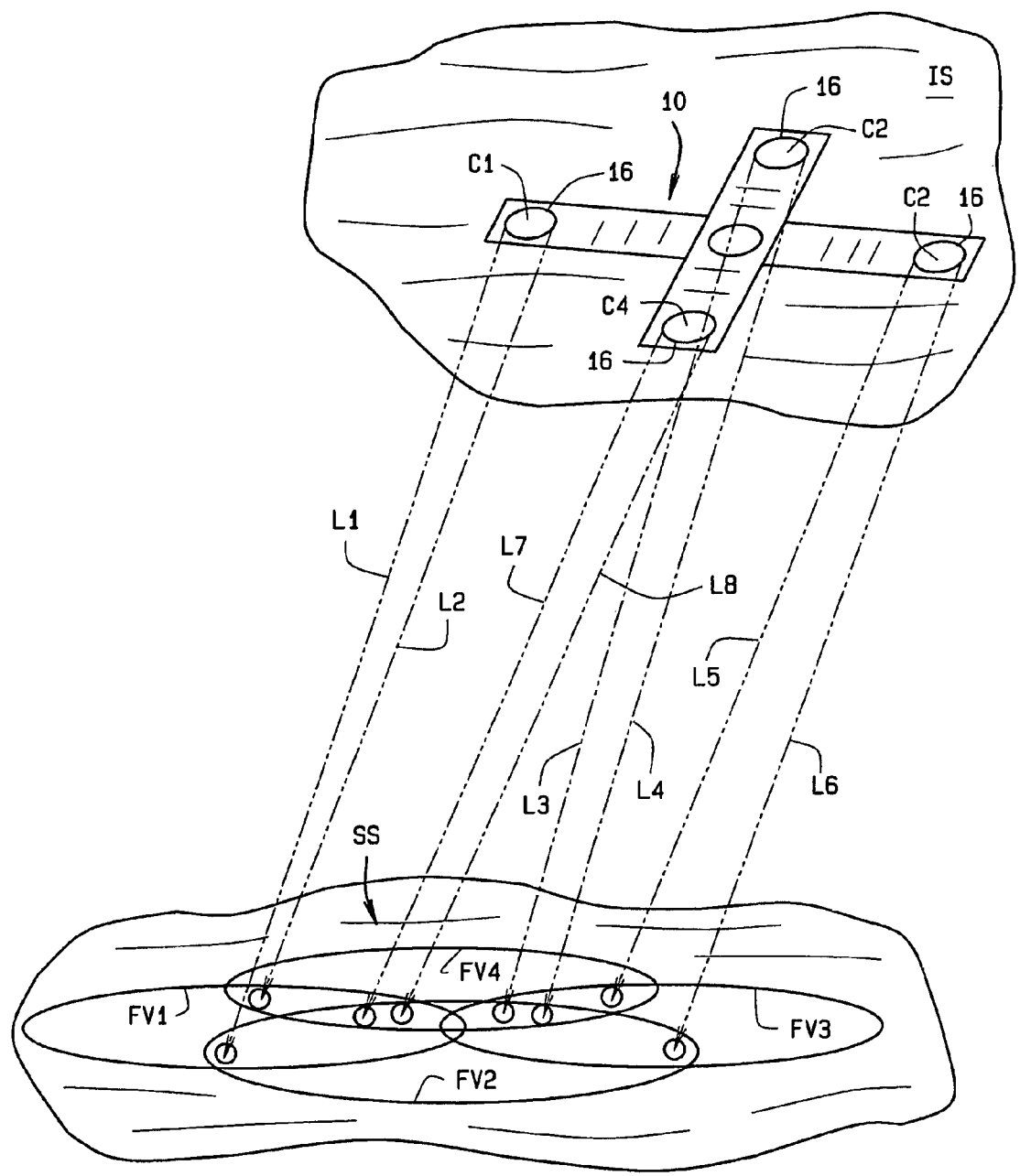
FIG. 5 is a schematic drawing showing the platform positioned within a cavity with the transceivers illuminating a surgical site within the cavity.

FIG. 5 shows a platform 10 anchored to the inner surface IS of a patient cavity. The devices 16 for the platform are camera devices, and are denoted as cameras C1-C4. In the camera devices, the pixel array 26 comprises, for example, a CCD or CMOS camera which is surrounded by the lasers L and illuminating devices to illuminate the surgical site SS. For purposes of clarity, the devices are each shown with only two lasers. The actual device would include many lasers. The reflected light from the illuminating devices is received by the pixel array of the cameras and then transmitted to the CPU 18 to be displayed on the display 20.

As seen in FIG. 5, each camera transceiver C1-C4 illuminates a field of view $FV_1$-$FV_4$, with the fields of view of each camera overlapping the field of view of at least one other camera. The MEMS for each of the transceivers can be controlled to alter the position of the transceivers such that the field of view of one camera overlaps the field of view of at least one other camera. In certain circumstances, it may be desirable to have the cameras having generally parallel (i.e., non-overlapping) fields of view. The MEMS in such circumstances would then be controlled to position the cameras for the desired angle and field of view. The CPU 18 receives the signals from the cameras and "stitches" the images together to provide a combined view or image of the surgical site, which is then displayed on the display 20.

The device lasers or LEDs emit light (in the form of laser beams or IR energy), and the light reflects off the surgical site within the field of view of the cameras to be detected by the pixel arrays 26 of the cameras. While the field of views of the several cameras preferably overlap each other, the cameras (i.e., sensors) can be positioned such that the field of view of one or more cameras is parallel or even perpendicular to the field of one or more other cameras.

The device includes many lasers or LEDs, however, for purposes of clarity, two laser beams per device are shown, and are labeled $L_1$-$L_8$. As shown laser beams $L_1$ and $L_2$ are associated with camera C1; laser beams $L_3$ and $L_4$ are associated with camera C2; laser beams $L_5$ and $L_6$ are associated with camera C3; and laser beams $L_7$ and $L_8$ are associated with camera C4. The laser beams from each camera target the surgical site SS within the field of view of the particular camera. Thus, for example, laser beams $L_1$ and $L_2$ are within the field of view $FV_1$ of camera C1. In addition, the laser beams of a particular camera are also within the field of view of at least one additional camera. Thus, as seen in FIG. 5, the laser beam $L_1$ of camera C1 is within the filed of view $FV_4$ of camera C4; and the laser beam $L_2$ of camera C1 is within the field of view $FV_2$ of camera C2. The two laser beams of camera C1 are shown to be in the field of view of different cameras (as well as in the field of view $FV_1$ of camera C1). However, the laser beams could both also be in the field of view of the same additional camera. For example, the laser beams $L_3$ and $L_4$ of camera C2 are both within the field of view $FV_3$ of camera C3. They are also both within the field of view $FV_4$ of camera C4. The table below shows the fields of view in which each of the lasers target the surgical site SS.

| Laser | Field Of View 1 | Field Of View 2 | Field Of View 3 | Field Of View 4 |
|---|---|---|---|---|
| $L_1$ | X | X | | |
| $L_2$ | X | | | X |
| $L_3$ | | X | X | X |
| $L_4$ | | X | X | X |
| $L_5$ | | | X | X |
| $L_6$ | | X | X | |

-continued

| Laser | Field Of View 1 | Field Of View 2 | Field Of View 3 | Field Of View 4 |
|---|---|---|---|---|
| $L_7$ | X | X |   | X |
| $L_8$ | X | X |   | X |

Thus, each laser is seen by at least two cameras, and each camera sees at least two laser beams. The laser beams are used to perform two functions. First, the laser beam can be used to measure distances. The distance measured would be the distance between the laser source (i.e., the camera) and the laser target point in the surgical site SS. As noted, each device 16 includes many lasers. The number of lasers, in conjunction with the number of pixels in the sensor arrays 26 allows for the surgical site to be rasterized and for a detailed 3-dimensional image of the surgical site to be produced. Because the distances measured can be highly precise (i.e., within 1/1000000" or $10^{-6}$") the 3-dimensional image or map of the surgical site can be quite accurate.

The lasers are also be used to align the images produced by two different cameras to form a unified image from the images transmitted by the several cameras and to maintain the alignment of the images. As noted, each laser beam is "seen" by at least two different cameras. When the camera "sees" a laser beam, the laser beam is detected by a particular pixel or group of pixels in the sensor pixel array 26. The same laser image will be "seen" or detected by a particular pixel or group of pixels in two or more cameras. The information from the different cameras is transmitted to the CPU. The CPU, in processing the information from the different cameras, will determine which portions of the two images correspond to the laser spot. In this way, the computer can determine which portions of the adjacent fields of view overlap, and can join or "stitch" together the images from the several cameras using the position of known laser spots as a guide to form a single image which will then be displayed on the display 20. To properly join together the images from the different cameras together, the CPU 18 will have to be able to differentiate the different laser beams. The laser beams can be differentiated in several ways. One method is to operate the lasers at different wavelengths. The CPU can then match the laser spots together based on the wavelength (color) of the laser spots on the image data received from each sensor 26.

Alternatively, different frequencies can be used. For example, different frequencies of red, green and blue light, as well as different frequencies of infrared light, can be emitted by the transmitters. In addition, a black and white sensor can be provided which can switch back and forth at a rate of many times per second. The different frequency lights can be timed to pulse at different times, and the sensor can be timed to the pulses, such that the sensor will sense the pulses in a repeating pattern, e.g., red, green, blue, red, green, blue, etc. The different frequencies can be aimed or focused at different points in the surgical site, providing for different markers in the surgical site. The computer would use the information from the cameras as described above, but would have several different markers from which to determine the image alignment.

As noted above, the position of a camera may change relative to the position of the surgical site SS. This can be due to movement of the inner surface IS of the cavity wall or due to manipulation of objects (i.e., organs, tissue, etc.) at the surgical site. The laser beams, as noted, are received by specific pixels within the sensor arrays 26 of the cameras. When the relative position between a camera and the surgical site is changed, the image or field of view of the camera is affected.

If the unified image (as just described) is not updated, and simply the images of the cameras are shown, there will be a disconnect in the image seen on the display 20—that is, the image will not be a unified image. In order to maintain the image displayed on the display 20 as a unified image, the CPU 18 will process the image data received from the sensors (as described above) in real time, and, in real time, update the image displayed on the display. If necessary, the CPU can also control the MEMS 24 to alter the relative position of the transceiver 22 if necessary. This may be required, for example, if the movement at the surgical site or movement of the cavity wall alters the field of view of a particular camera, such that the field of view of the particular camera does not overlap the field of view of at least one other camera. By adjusting the position of the camera, its field of view can be changed so that the camera will again "see" a laser beam from one of the other devices 16, such that the image data can be processed, as discussed above, to produce and maintain a unified image which can be displayed on the display 20.

The cameras can, instead of relying on the laser, rely on a specific target on the surgical site and within the field of view of the cameras, to maintain alignment between the images produced by the different sensors to produce the unified image displayed on the display 20. Such a target can be a natural target (i.e., part of the physiology of the surgical site). Alternatively, the target can be an item which is positioned within the surgical site and within the field of view of the cameras. Such a target could be one or more small dots which are positioned in the surgical site. In the former case, specific portions of the surgical site SS will be viewed by specific pixels in the pixel array 26 of each transceiver. In the latter case, the target will be viewed by specific pixels in the pixel array 26. When the relative position of the transceiver and the surgical site changes, the field of view of the transceiver will change and the specific pixels which view the target will change. This change in the pixels which receive the information regarding the target will be received by the CPU 18, and the CPU can control the position of the transceivers via the transceivers' associated MEMS such that the target will be received by the original pixels in the pixel array 26.

The intra-corporeal data will preferably be "real time" data. Although "real time" would preferably be substantially instantaneous, it is realized that there will be some delay in the receipt of the image data, the processing of the image data, and the ultimate displaying of an image on the display 20. While the intra-corporeal data is all preferably real time, it will be recognized that the extra-corporeal data may not be real time. For example, if the extra corporeal data includes x-ray, CT scan and/or MRI data, such data most likely will not be in real time. However, extra-corporeal data, such as ultrasound data could be in real time. In either event, in order to overlay the extra-corporeal data with the intra-corporeal data, the extra-corporeal image data must be aligned with the intra-corporeal image data. To do this, there must be a reference point or target that is common between the two sets of data. The platforms 10 can be used as targets. The platforms will appear on the extra-corporeal image data, and the position of the platforms can be determined using the intra-corporeal image data. Alternatively, targets in the surgical site can be used to align the extra-corporeal image data with the intra-corporeal image data. Such surgical site targets can include a physiological condition at the surgical site or a target which is placed at the surgical site.

The CPU can process the image data from the sensors in real time and to join or "stitch" together the images data in real time and can individually control the MEMS of the separate devices to maintain an overlap of the field of views for the cameras. This allows for the CPU to maintain a unified image which is displayed on the display 20, and the images from one camera will not become disjointed or disconnected from the images of another camera. Hence, the surgeon will be presented with a field of view on the display 20 which will not be suddenly changed due to relative movement of either the surgical site or the platform. As can be appreciated, providing the surgeon with a substantially stable image will facilitate the surgical procedure.

The imaging system is shown in FIG. 5 with transceivers which illuminate the surgical site and then transmit the image data to the CPU for display on the display 20. That is, the transceivers transmit and receive energy in the optical light range. The transceivers, however, can transmit and receive other forms of energy as well. For example, and without limitation, the transceivers can transmit and/or receive energy enabling the imaging system to gather thermal, ultrasonic, Doppler, infrared, and/or spectrographic (for tissue density information) information, in addition to the optical (or RGB) information. These transceivers are all providing intra-corporeal data. As discussed below, the system can also accept extra-corporeal information, such as x-ray, CT scan, MRI scan information and ultrasound information, for example. The different types of intra-corporeal and extra-corporeal information noted is exemplary only. It will be appreciated that other types of data can be gathered both intra-corporeally and extra-corporeally, and images can be formed from this intra- and/or extra-corporeal data. The information gathered can be used to produce images which consist solely of selected information—i.e., solely optical (as described above), solely ultrasonic, solely thermal, etc. Alternatively, the imaging system can overlay one set of information over another set of information to produce a composite image on the display 20. For example, a thermal energy map or image (which may, for example, disclose blood vessels beneath the surface seen in the optical light image) can be layered over the optical light image. Additionally, intra-corporeal data can be layered over extra-corporeal data or information. This overlaying of information will then enable a surgeon to "see" below the surface of the surgical site. The thermal image (in this example) will be "stitched" together, or joined with, the RGB or optical image, using the lasers, as discussed above. In this manner, the thermal image will be aligned with the RGB image so that the surgeon can see the thermal data of a particular portion of the surgical site laid over the RGB image of the same portion of the surgical site. The different energy scans can be used in conjunction with each other to, for example, inform the surgeon the how far below the surface of the surgical site a blood vessel or other organ or structure is located.

To enable the overlaying of the different energy scans to produce a composite image on the display 20, the various transceivers which allow for the different energy scan will need to be positioned within the patient cavity. To this end, different devices can be placed on a single platform. For example, a single platform can be provided with thermal devices, optical light (or RGB, IR, laser, etc.) devices, ultrasonic devices, etc. Hence, the platform can be provided with a desired set of different device types to enable a platform to be used to produce scans of different energy types. Alternatively, a platform can be provided with a single device type, and then multiple platforms (each with different device types) can be positioned within the patient cavity.

The devices used to produce the various different scans or images would, like the optical light (RGB) device shown in FIG. 4 and described above, include a pixel array surrounded by lasers (at least some of which will transmit laser energy). However, the pixel array for the selected transceiver can be one which will detect energy emitted from the surgical site itself. For example, a transceiver which can be used to gather thermal energy information will include a sensor which can detect thermal energy, and the sensor will be surrounded by lasers, as described above, to facilitate the alignment of the scan with the scan of other transceivers. Because the thermal energy emanates from the surgical site, the transceiver which gathers thermal information will not necessarily require energy transmitters (other than the laser transmitters). On the other hand, a transceiver which is used to gather ultrasonic information would have a central sensor adapted to receive ultrasonic energy and transmitters surrounding the pixel array which transmit ultrasonic energy. The ultrasonic transceiver would also include lasers to facilitate alignment of the ultrasonic information with the information from other transceivers. This will allow for the ultrasonic image or thermal image, for example, to be laid over the optical image, to produce the composite image, as described above. A transceiver can also include multiple sensors, so that a single transceiver could, for example, sense both optical and thermal energy.

To facilitate the surgical procedure, the information gathered by the transceivers and displayed on the display will be gathered and displayed in real time. To enable real time display, the transceivers gather information and transmit the information to the CPU at a rate equivalent to 60 frames/second. The transceiver lasers also fire at a rate of 60 frames (or times) per second. This laser firing rate allows for the lasers to be used for targeting and tracking (as described above) at a rate of millions of times per second. This results in a significant amount of data (e.g., 8 megabits/second) that is being received by the CPU from the transceivers. Thus, the CPU will need to be robust enough to receive and process this amount of information.

In a surgical procedure in which the imaging system of the present invention is used, at least one incision will be made in the patient's body to access or form a cavity in said patient's body. An accessed cavity would include, for example, the patient's abdominal or thoracic cavity. A formed cavity would include, for example, a cavity made adjacent a patient's spine, throat, etc. by the use of lifters. An instrument platform is inserted into the cavity and anchored to a surface of the cavity. As discussed above, the platform will include a plurality of transmitters and a plurality of receivers which emit and receive energy, respectively, enabling the instrument to transmit data to a computing device. The data is chosen from the group consisting of optical lighting, thermal, ultrasonic, infrared, Doppler, spectrographic, distance, and combinations thereof. Further, as noted above, this intra-corporeal data can be supplemented with extra-corporeal data such as x-ray data, CT scan data, MRI scan data, ultrasound data, etc.

The transmitters are activated to direct energy to structures within the cavity, and the receivers detect or receive energy reflected from the structures. The receivers then transmit the data which is indicative of the relative position of the structures within the cavity to the computing device. The data that is transmitted is image data in a rasterized format.

As noted above, the computer can control the position of the receivers as necessary to maintain the receivers in an aligned state as the cavity wall (to which the instruments are anchored) and the structures with the cavity move or are moved relative to each other.

The computer converts the data to a visual format and transmits the visual format to a display to enable a practitioner (such as a surgeon) to view the image of the surgical site in real time. Although ideally, real time transmission of data would enable the practitioner to view instantaneously any changes at the surgical site or within the cavity. However, one skilled in the art will understand that "real time" viewing allows for a slight delay between the detecting of the image data and the displaying of the image. The ability for the computer to alter the control the position or angle of the receivers will reduce or eliminate any disconnect in the viewed image due to movement of the instrument (by movement of the cavity wall) or movement of the structures within the cavity. The ability for the practitioner to view the surgical site in real time allows the practitioner to direct instruments within the cavity to perform a surgery without haptic sense, but by the data received from the sensors.

If desired, the practitioner can insert a separate camera into the cavity which can be used as a rover camera or moved to a desired position within the cavity. This extra camera will also be in communication with the computing device and transmits information to the computing device. The computing device will then align the view of the separate camera with the cameras of the platform or combine the information from the separate camera with the platform cameras to provide additional information to the surgeon. Also, as noted above, the practitioner can supplement the intra-corporeal data with extra-corporeal data.

As various changes could be made in the above constructions without departing from the scope of the invention, it is intended that all matter contained in the above description or shown in the accompanying drawings shall be interpreted as illustrative and not in a limiting sense.

The invention claimed is:

1. A method of facilitating minimally invasive surgery on a patient; the method comprising:
    a) forming at least one incision on said patient's body to access a cavity within said patient's body, said incision passing through a cavity wall;
    b) inserting an instrument platform into said cavity through said incision; said platform carrying a plurality of transmitters and a plurality of receivers; said transmitters and receivers emitting and receiving energy enabling said instrument to transmit image data collected intra-corporeally;
    c) anchoring said platform to an interior surface of said cavity wall proximate said incision, with said plurality of transmitters and receivers having a field of view directed into said cavity and away from said interior surface on which said platform is anchored;
    d) activating said transmitters to direct energy to structures within said cavity; said receivers receiving energy reflected from the structures within said field of view of said receivers and transmitting intra-corporeal data indicative of the relative position of said structures to said computer; said transmitted intra-corporeal data being chosen from the group consisting of optical lighting, thermal, ultrasonic, infrared, Doppler, x-ray, spectrographic, distance, and combinations thereof;
    e) said computer altering the field of view of said receivers based on the intra-corporeal data received from said receivers as necessary to maintain said receivers in an aligned state as said cavity wall and said structures move or are moved relative to each other; and
    f) converting said intra-corporeal data to a visual format enabling a surgeon to view said visual image of the cavity in real time.

2. The method of claim 1 wherein said method further comprises collecting data extra-corporeally and transmitting said extra-corporeally collected data to said computer; said computer aligning said extra-corporeally collected data with said intra-corporeally collected data to generate an aligned composite data set representative of internal tissues and structures within said patient's body.

3. The method of claim 2 wherein said extra-corporeally collected data is chosen from one or more of X-ray data, CT scan data, MRI scan data, ultrasound data and combinations thereof.

4. The method of claim 2 wherein the method additionally includes overlaying at least one type of extra-corporeally collected data acquired from a separate sensor with at least one type of intra-corporeally collected data in an aligned overlayed format.

5. The method of claim 1 wherein the method additionally includes generating a display of said visual format, said visual format converted from two or more types of said intra-corporeally collected data aligned in an overlayed format.

6. The method of claim 1 wherein said computer updates said displayed information in real time, thereby enabling a surgeon to direct instruments within the cavity to perform a surgery without haptic sense, but by the data received from the sensors.

7. The method of claim 1 including inserting a separate camera into the cavity which can be used as a rover camera or moved to a desired position within the cavity; the camera being in communication with said computing device and transmitting information to said computing device; said computing device aligning the field of view of the separate camera with the field of view of said receivers or combining the information from the camera with the data received from said receivers to provide additional information to the surgeon.

8. A method of facilitating minimally invasive surgery on a patient; the method comprising:
    a) forming at least one incision on a patient's body to access a cavity of said patient's body, said incision passing through a cavity wall;
    b) inserting an instrument platform into said cavity; said platform carrying a plurality of cameras and at least one light source; said cameras being in communication with a computing device; said cameras being movably mounted to said platform, the position of said cameras being controlled by said computer;
    c) anchoring said platform to an interior surface of said cavity wall proximate said incision with each of said cameras having a field of view directed into said cavity and away from said interior surface onto which said platform is anchored;
    d) said cameras transmitting optical image data to said computing device;
    e) displaying said image data in real time on a display;
    f) altering a field of view of said cameras based on the image data received from said cameras as necessary to maintain image data from said cameras in an aligned state as said cavity wall and said structures move or are moved relative to each other
    g) said computing device altering the position of said cameras based instructions received by an operator; whereby the field of view of the cameras can be made to be parallel, perpendicular, or overlapping.

9. The method of claim 8 wherein said step of altering the field of view of said cameras comprising a step of maintaining a predetermined area of the camera's field of view on a marker to maintain physical alignment of cameras, lasers, and other sensors and targeting and tracking devices, allowing the information independently received from said cameras, sensors, targeting devices, and tracking devices to be aligned.

10. The method of claim 9 wherein the marker comprises a laser beam illumination point or a physical target placed in a desired position in the cavity.

11. The method of claim 8 wherein said step of altering said field of view of said camera comprises allowing the cameras' fields of view to be moved by an optical device to be parallel, perpendicular, or overlapping.

12. The method of claim 11 wherein said camera incorporates a plurality of MEMS components; the step of altering the field of view of said cameras comprising controlling the MEMS components of the camera.

13. An imaging system for providing practitioners with an image of a surgical site within a patient's body cavity during minimally invasive surgery; said imaging system comprising:
  a) a plurality of sensors and transmitters adapted to be anchored to a wall of said body cavity; said transmitters being operable to emit a selected form of energy towards the surgical site; said energy being chosen from one or more of the following: optical, thermal, ultrasonic, infrared, Doppler, spectrographic, distance, and combinations thereof; said plurality of sensors comprising laser sensors which detect laser energy and energy sensors which energy transmitted by said transmitters; and said energy sensors adapted to receive reflected energy from within an associated field of view of the surgical site; said energy sensors configured to transmit data representative of intra-corporeal images of the received reflected energy from within the associated field of view; said data being chosen from one or more of the following: optical information, thermal information, ultrasonic information, infrared information, Doppler information, spectrographic information, distance information, and combinations thereof;
  b) a plurality of lasers operable to direct associated laser beams towards the surgical site; said laser sensors configured to detect laser energy reflected from the surgical site within said associated fields of view;
  c) a means for converting the transmitted data from the laser and energy sensors into image data;
  d) a means for comparing the image data from two or more laser sensors having at least partially overlapping fields of view to identify detected laser energy within said image data to align the image data to produce a single unified image representative of said surgical site within the associated partially overlapping fields of view; and
  e) means to maintain the lasers in relative position to each other.

14. The imaging system of claim 13 including means for receiving extra-corporeally collected image data; means for aligning said extra-corporeally collected image data with intra-corporeally collected image data; and means for producing a composite image containing both said intra-corporeally collected image data and said extra-corporeally collected image data in an aligned and overlayed image format.

15. The imaging system of claim 13 wherein said plurality of lasers include a Vertical Cavity Surface Emitting Laser.

16. The imaging system of claim 13 including means for overlying the two different types of data to form a composite image.

17. The imaging system of claim 13 including means for determining the position of objects within said field of view at the surgical site.

18. The imaging system of claim 13 wherein said lasers are used to determine distance data associated with objects and surfaces within said field of view of said sensors.

19. The imaging system of claim 18 wherein said distance data is combined with selected other data to provide a 3-dimensional map of the surgical site.

20. The imaging system of claim 13 wherein the data is updated in real time, said system comprising means for displaying selected data in real time.

21. The imaging system of claim 20 including means for determining distances between and relative positions of surgical instruments and selected areas of a surgical site to facilitate one or more surgical tasks selected from a set of tasks including, cutting, sewing, and stapling.

22. The imaging system of claim 13 further includes a processing system configured with software to interpret the data from said sensors; said software including means for processing the sensor data to produce one or more images selected from a set of images including:
  a) Multiple views;
  b) Distal & Proximal views;
  c) Combination of panoramic views;
  d) Panoramic views;
  e) Ometry views where the data is used for measuring exact distances; and
  f) Ometry views where the data is used to replace haptic sensing.

* * * * *